(12) United States Patent
Puntambekar et al.

(10) Patent No.: US 10,921,313 B2
(45) Date of Patent: *Feb. 16, 2021

(54) POINT OF CARE TESTING ASSAY SYSTEM USING NOVEL MICROFLUIDICS

(71) Applicant: micobiomed., Ltd, Seoul (KR)

(72) Inventors: Aniruddha Puntambekar, Mason, OH (US); Jungyoup Han, Cincinnati, OH (US); Junhai Kai, Loveland, OH (US); Chong Ahn, Cincinnati, OH (US)

(73) Assignee: micobiomed., Ltd, Seongnam-si (KR)

( * ) Notice: Subject to any disclaimer, the term of this patent is extended or adjusted under 35 U.S.C. 154(b) by 221 days.

This patent is subject to a terminal disclaimer.

(21) Appl. No.: 14/414,945

(22) PCT Filed: Jul. 16, 2013

(86) PCT No.: PCT/US2013/050681
§ 371 (c)(1),
(2) Date: Jan. 15, 2015

(87) PCT Pub. No.: WO2014/014911
PCT Pub. Date: Jan. 23, 2014

(65) Prior Publication Data
US 2015/0177233 A1    Jun. 25, 2015

Related U.S. Application Data (60) Provisional application No. 61/672,003, filed on Jul. 16, 2012.

(51) Int. Cl.
*G01N 33/53* (2006.01)
*B01L 3/00* (2006.01)
*G01N 35/00* (2006.01)

(52) U.S. Cl.
CPC ........ *G01N 33/5302* (2013.01); *B01L 3/5027* (2013.01); *B01L 2200/10* (2013.01); *G01N 2035/00158* (2013.01)

(58) Field of Classification Search
CPC ...... G01N 33/5302; G01N 2035/00158; B01L 3/5027; B01L 2200/10
See application file for complete search history.

(56) References Cited

U.S. PATENT DOCUMENTS

| | | | | |
|---|---|---|---|---|
| 7,160,025 B2* | 1/2007 | Ji | ...................... | B01F 5/0646 366/341 |
| 2002/0191864 A1* | 12/2002 | Lennon | ............... | H01J 49/0418 382/288 |
| 2003/0011701 A1* | 1/2003 | Nilson | ................. | A61B 5/0059 348/370 |
| 2004/0252584 A1* | 12/2004 | Ji | ..................... | B01F 5/0646 366/341 |
| 2006/0051250 A1* | 3/2006 | Gonzalez | ............. | B01L 3/0268 422/400 |
| 2007/0003448 A1* | 1/2007 | Kanigan | ............... | B01L 3/0244 422/400 |
| 2007/0231217 A1* | 10/2007 | Clinton | .............. | G01N 35/1081 422/119 |
| 2008/0281471 A1* | 11/2008 | Smith | ................. | B01F 13/0071 700/266 |
| 2010/0285490 A1* | 11/2010 | Dees | ................. | G01N 33/54373 435/7.1 |
| 2011/0070581 A1* | 3/2011 | Gupta | ............. | G01N 33/56972 435/5 |
| 2012/0152050 A1* | 6/2012 | Richardson | ............. | B25J 9/023 74/490.02 |
| 2013/0171679 A1* | 7/2013 | Lee | ........................ | C12M 23/16 435/29 |
| 2014/0358060 A1* | 12/2014 | Laster | ..................... | A61M 1/38 604/6.09 |

* cited by examiner

*Primary Examiner* — Ann Y Lam
(74) *Attorney, Agent, or Firm* — Dinsmore & Shohl LLP; Yongsok Choi, Esq.

(57) ABSTRACT

A point of care testing assay system for determining the presence and/or amount of an analyte of interest in a sample, and methods for using such assay system, are disclosed. The system comprises a microfluidic means capable of performing testing with low sample volume in a sample matrix, and having high sensitivity and substantially a 5-log wide dynamic range and capable of performing an assay in approximately fifteen minutes, and in which the microfluidic means comprises a microfluidic testing cartridge with associated electronics, a precision pipettor, a high sensitivity detection module, a motion stage, and an on-board electronics display means that can be read by a user as an indication of the presence and/or amount of the analyte in the sample.

6 Claims, 6 Drawing Sheets

FIG. 1

Exterior

Interior

POINT OF CARE TESTING ASSAY SYSTEM USING NOVEL MICROFLUIDICS

CROSS REFERENCE TO RELATED APPLICATION

This application is a non-provisional application, which incorporates by reference herein and claims priority, in part, of U.S. Provisional Application No. 61/672,003, filed Jul. 16, 2012.

BACKGROUND OF THE INVENTION

The present invention relates generally to diagnostic assay systems and methods, and in particular relates to a portable Point of Care Testing (POCT) assay system incorporating and improving upon the microfluidic immunoassay technology described and claimed in co-assigned and co-pending U.S. patent application Ser. No. 13/384,963 and PCT Patent Application No. PCT/US10/42506, the disclosures of each of which have been incorporated by reference herein, and which is capable of performing point of care (such as in a hospital bedside or small clinic setting) testing with low sample volume, a complex sample matrix (such as whole blood), and with such characteristics as high sensitivity and wide dynamic range.

BRIEF DESCRIPTION OF THE INVENTION

Figure 2:
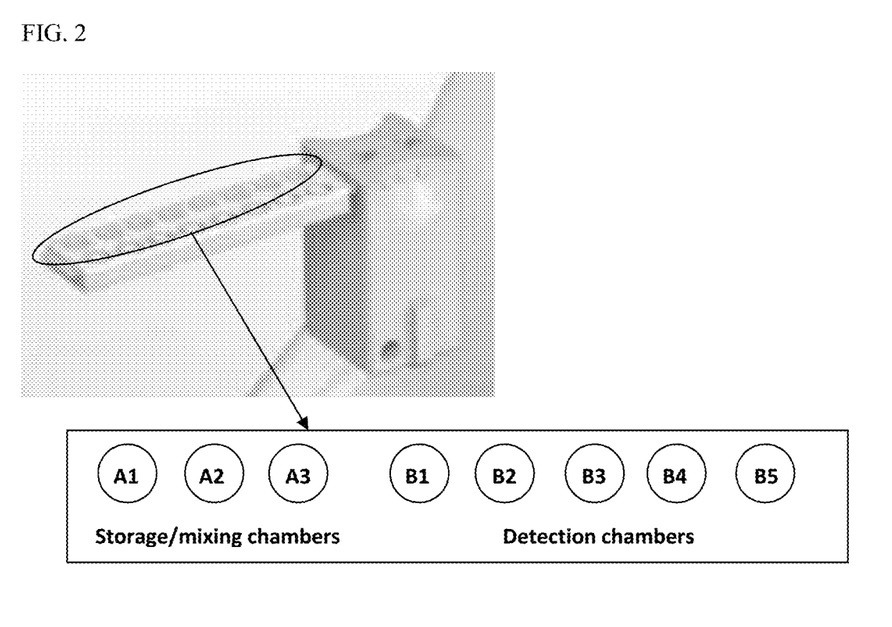
FIG. 2 shows the assay system of a preferred embodiment of the present invention wherein five detection chambers and three storage reservoirs are positioned in a configuration conforming to the ANSI/SBS standards for microplate well positions.

Referring now to the drawing figures incorporated herein, which illustrate preferred embodiments of the present invention but which are in no way intended to be limiting to the scope of the present invention:

A preferred test cartridge embodiment is shown in FIG. 2, wherein five detection chambers and three storage reservoirs are positioned in a configuration conforming to the ANSI/SBS standards for microplate well positions.

An alternate preferred embodiment of the test cartridge contains up to twelve "well" positions some wells are used storage reservoirs and some wells are used as detection chambers conforming to the ANSI/SBS standards for microplate well positions.

In an alternate preferred embodiment, one or more of the detection and/or reservoir "wells" do not conform to the ANSI/SBS standards for microplate well positions.

In an alternate preferred embodiment, the test cartridge has four detection chambers and four storage reservoir wells. This configuration is particularly well suited for a two-step dilution process allowing for extended dilution capability and consequently wide dynamic range measurement.

In another alternate preferred embodiment, the test cartridge has ten detection chambers and three storage reservoir wells, furthermore wherein the detection chambers and storage reservoirs wells are arranged in the same linear footprint but do not confirm to the ANSI/SBS standard for microplate well positions. This configuration is particularly well suited for detection of up to eight analytes.

In yet another embodiment, the test cartridge has six storage reservoir wells and five detection chambers, furthermore wherein the detection chambers and storage reservoirs wells are arranged in the same linear footprint but do not confirm to the ANSI/SBS standard for microplate well positions. This configuration is particularly well suited for separate storage of the multiple detection antibodies.

Many variations and modifications are within the scope of additional preferred embodiments of the invention, for example wherein the number of detection chambers and/or storage reservoirs is more or less than the design shown in FIG. 2, and all such variations and modifications are intended to be within the scope of the invention as described herein.

In addition, in a preferred embodiment, the horizontal motion stage is a single axis stage.

In an alternate preferred embodiment a X-Y stage can be used to enable greater flexibility in system operation.

In yet another preferred embodiment the single axis stage can be a pulley driven system.

All variations and modifications utilized in the present invention to transport the test cartridge precisely to desired locations with respect to the pipetting head, reader module and other locations are intended to be fully within the scope of the invention as disclosed herein.

DETAILED DESCRIPTION OF THE INVENTION

A preferred assay protocol performed in accordance with the present invention is described herein wherein the sample (diluted or otherwise) is pre-mixed with the detection antibody solution and then the mixture loaded into the detection chamber. However, it is to be appreciated by one skilled in the art that in an example of one alternate protocol method of use of the invention, the sample can be first loaded to the detection chamber, then after suitable incubation duration the wash buffer solution can be added and after yet another suitable incubation duration the detection antibody solution can be added. This method may be particularly advantageous for assays having the potential of incurring the so called "hook effect" wherein analyte (or antigen) concentrations may lead to falsely reduced signals.

A significant benefit of the POCT assay system provided by the present invention is the ability to "tune" the assay sensitivity, simply by modifying the assay protocol with increased or fewer sample loading steps to affect assay sensitivity.

Another significant benefit of the POCT assay system approach provided by the present invention is the ability to detect an analyte of interest across an extremely broad dynamic range.

Yet another significant benefit of the POCT assay system approach of the present invention, specifically wherein the detection chamber of the test cartridge is substantially similar to one well and associated microfluidic channel in a conventional microplate, or in a microplate such as described in U.S. patent application Ser. No. 13/384,963, is the ability to simulate point of care assay performance using conventional microplate automation instrumentation.

Even another significant benefit of the POCT assay system approach of the invention described herein, specifically wherein the detection chamber of the test cartridge is substantially similar to that of a conventional microplate, or of a microplate such as described in U.S. patent application Ser. No. 13/384,963, is the ability to develop and optimize assays on such microplate platform, and due to the configuration of the detection chamber thereby enable substantially similar performance of the assay in the test cartridge in the POCT assay system of the invention.

Figure 1:
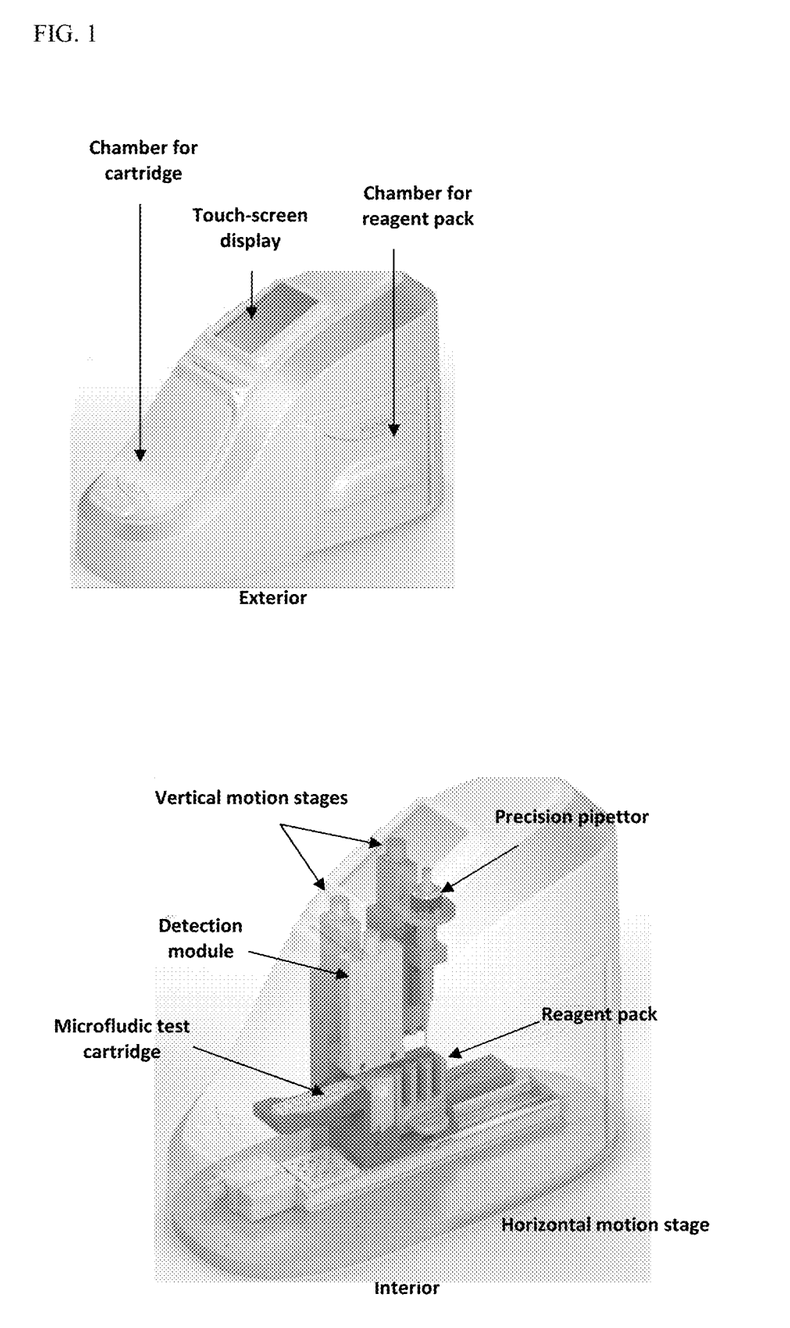
FIG. 1 shows the assay system of a preferred embodiment of the present invention which comprises a portable Point of Care Testing (POCT) assay system incorporating and improving upon the microfluidic immunoassay technology described and claimed in co-assigned and co-pending U.S. patent application Ser. No. 13/384,963 and PCT Patent Application No. PCT/US10/42506, the entire disclosures of each of which are hereby incorporated by reference herein.

Referring now in more detail to the drawings, as shown in FIG. 1, the assay system of the present invention comprises a portable Point of Care Testing (POCT) assay system incorporating and improving upon the microfluidic immunoassay technology described and claimed in co-assigned and co-pending U.S. patent application Ser. No. 13/384,963 and PCT Patent Application No. PCT/US10/42506, the disclosures of each of which have been incorporated by reference herein, and which is capable of performing point of care (such as a hospital bedside or small clinic setting) testing with low sample volume, complex sample matrix (such as whole blood), and with such characteristics as high sensitivity and 5-log wide dynamic range, in approximately fifteen minutes. The system consists of a microfluidic test cartridge with associated "smart" electronics, a precision pipettor, a high sensitivity detection module, a motion stage, and on-board electronics with a display that can be read by a user. One particularly preferred embodiment of the invention is illustrated in FIG. 1.

Smart microfluidic test cartridge: It contains multiple microfluidic based detection chambers, storage/mixing chambers and tips. It is disposable and will be replaced in each test. An example layout of detection chambers and storage/mixing chamber is shown in FIG. 2. The detection chambers will be pre-coated with capture antibodies to capture analyte. One storage/mixing chamber will contain lyophilized detection antibody(s). Referring to FIG. 2, which is an example of a chamber layout in a preferred embodiment of a microfluidic test cartridge of the present invention having a chamber containing portion extending therefrom, chambers A1 through A3, as graphically represented below, are storage/mixing chambers, and B1 through B5, also a graphically represented below, are detection chambers. As shown in FIGS. 2 and 4A through 4G, the top surfaces of the chambers A1 through A3 and chambers B1 through B5 are circularly shaped, equally sized, and linearly arranged on the microfluidic cartridge.

Reagent pack: It contains buffers and substrate. It will be placed in the system in the start of the day. It will be replaced either after certain amount of tests or time.

Precision Pipettor: The precision single channel pipettor will transfer reagents or samples to appropriate wells.

Detection module: It will be either fluorescence or luminescence high sensitivity detection module.

Motion stages: Motion stages will be used to move cartridge, pipettor and detector.

On-board electronics: The POCT assay system of the invention can be a standalone system controlled by the one-board electronics with, for example, a touch-screen display as a user interface. It can also contain all necessary ports for communication with other electronic devices, such as an associate personal computer or server. The system can also, in preferred embodiments, include a barcode or RF ID reader to identify the cartridge type.

System Operation

Figure 3A:
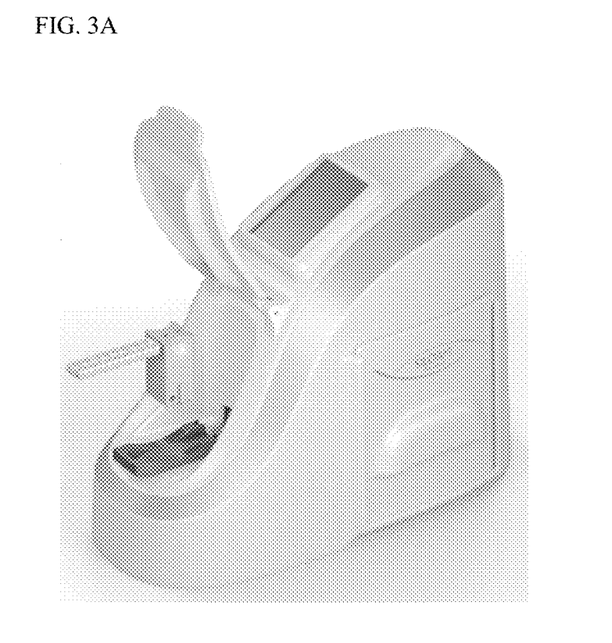
FIG. 3A illustrates a typical assay procedure in the performance of assays using a preferred embodiment of the present invention.
Figure 3B:
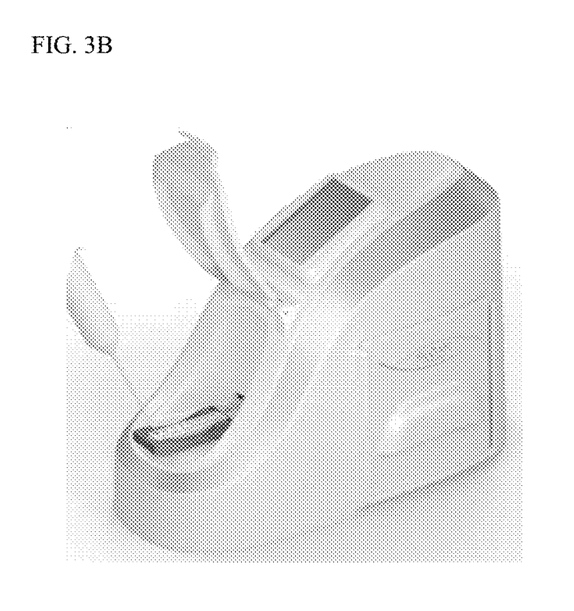
FIG. 3B illustrates a typical assay procedure in the performance of assays using a preferred embodiment of the present invention.
Figure 3C:
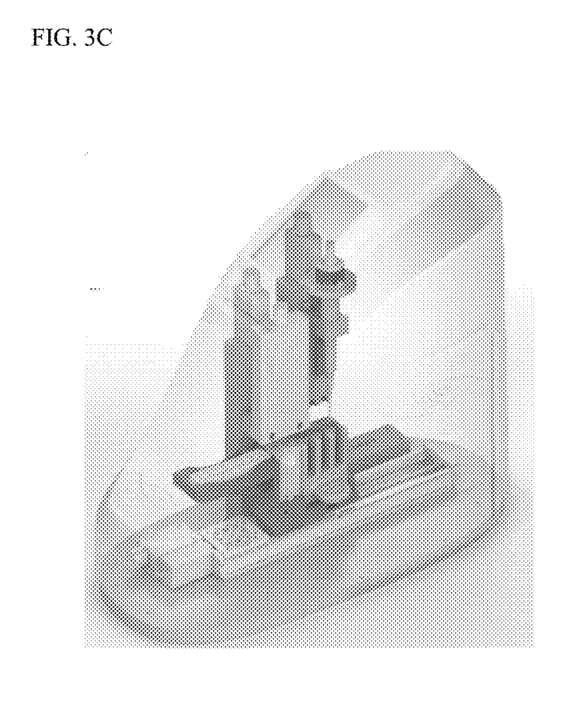
FIG. 3C illustrates a typical assay procedure in the performance of assays using a preferred embodiment of the present invention.

The POCT assay system of the present invention requires substantially minimal user intervention and operation, as illustrated in FIGS. 3A-3C. The buffer reagent will be placed in the system in the start of the day. For each test, as illustrated in FIGS. 3A-3B, the user will place the microfluidic testing cartridge into the system. Then the sample will be dispensed into the corresponding well of the cartridge. The assay type will be either selected by user in the touch-screen or obtained from barcode or RF ID. After pressing the start button, the motion stage will pull the cartridge into the system. The entire assay will be done by the system automatically and the result will be presented by means of a suitable display, such as a readout from an associated touch-screen LCD screen incorporated into the device, or other visible screen display such as in a laptop computer, at the end. A typical assay procedure in system is illustrated in FIGS. 3A-3C. FIG. 3A illustrates a typical user operation for a preferred POCT assay system of the invention, specifically, placing the microfluidic testing cartridge into the system. FIG. 3B depicts dispensing non-precise volume of sample to appropriate well. In FIG. 3C a start button is pressed, and the system runs the assay automatically and displays the result.

Figure 4A:
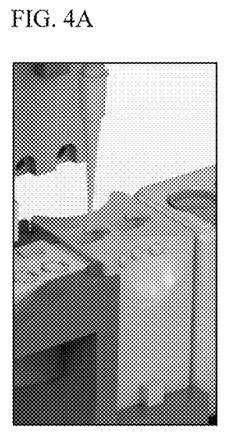
FIG. 4A illustrates a typical assay procedure performed utilizing a preferred embodiment of the POCT system of a preferred embodiment of the present invention.
Figure 4B:
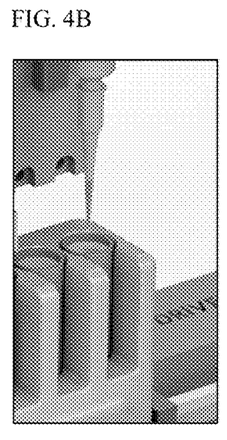
FIG. 4B illustrates a typical assay procedure performed utilizing a preferred embodiment of the POCT system of a preferred embodiment of the present invention.
Figure 4C:
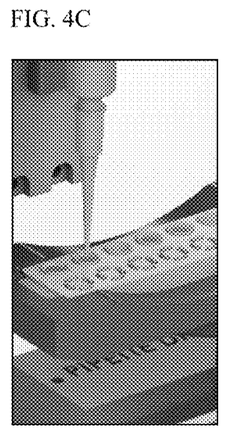
FIG. 4C illustrates a typical assay procedure performed utilizing a preferred embodiment of the POCT system of a preferred embodiment of the present invention.
Figure 4D:
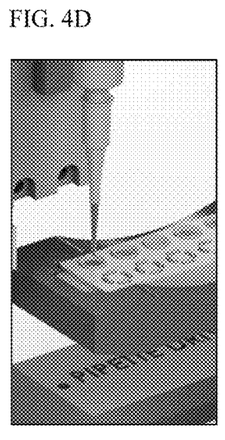
FIG. 4D illustrates a typical assay procedure performed utilizing a preferred embodiment of the POCT system of a preferred embodiment of the present invention.
Figure 4E:
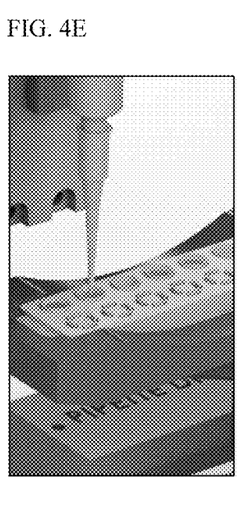
FIG. 4E illustrates a typical assay procedure performed utilizing a preferred embodiment of the POCT system of a preferred embodiment of the present invention.
Figure 4F:
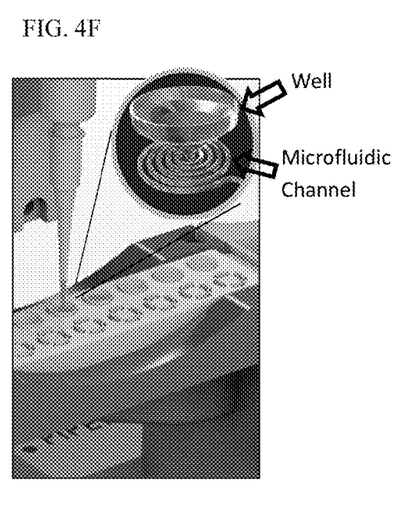
FIG. 4F illustrates a typical assay procedure performed utilizing a preferred embodiment of the POCT system of a preferred embodiment of the present invention.
Figure 4G:
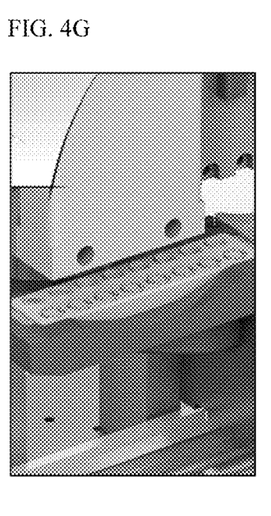
FIG. 4G illustrates a typical assay procedure performed utilizing a preferred embodiment of the POCT system of a preferred embodiment of the present invention.

Referring now to FIGS. 4A-4G of the drawings, a typical assay procedure in a preferred embodiment of the POCT system is shown. In FIG. 4A, a pipettor picks up the tip from the cartridge. In FIG. 4B, buffer is aspirated from a reagent pack. In FIG. 4C, the lyophilized detection antibody is reconstituted with the buffer. In FIG. 4D, the sample is aspirated sample. In FIG. 4E, the sample is mixed with reconstituted antibody. In FIG. 4F, the mixture is dispensed into the microfluidic detection chamber. As shown in FIG. 4F, the microfluidic detection chamber includes a well and a microfluidic channel connected to the well. The microfluidic channel is in spiral as shown in FIG. 4F. In FIG. 4G, after "flushing" with washing buffer and loaded with substrate (not shown in the drawing figure), the light intensity from the detection chamber is measured by a detector module as an indication of the analyte of interest in the sample.

Examples of Assay Run by POCT Assay System of the Present Invention

Single Analyte Assay—Cardiac Troponin

Cardiac troponin I (c-TnI) assay is used as a example to demonstrate a single analyte assay using a preferred embodiment of the POCT assay system of the invention. Only c-TnI will be measured in this assay with dynamic range within 2-log. Table 1 shows the layout of the chambers in the cartridge.

TABLE 1

Chamber layout for the cartridge in single analyte assay

| Storage/mixing chamber | | | Detection chamber | | |
|---|---|---|---|---|---|
| A1 | A2 | A3 | B1 | B2 | B3 |
| Well for Sample loading | Well contains lyophilized detection antibody | Well for mixing sample with reconstituted detection antibody | Detection chamber, pre-coated capture antibody | High control, pre-coated with high concentration anti-IgG antibody | Low control, pre-coated with low concentration anti-IgG antibody |

The detailed assay procedure is shown in Table 2. The sample will be mixed with reconstituted detection antibody then transferred into the detection chamber. A sandwich assay will be conducted in the detection chamber. The [analyte]-[enzyme conjugated detection antibody] complex will be captured by pre-coated capture antibody in microfluidic channel of detection chamber. Then the wash buffer will be loaded into the detection chamber to flush out the excess reagents Finally, the substrate will be loaded into the detection chamber and catalyzed by the enzyme conjugated on the detection antibody. The concentration of the analyte will be calculated based on light intensity with the stored calibration curve. Both control chambers pre-coated with anti-IgG antibody which will capture the enzyme conjugated detection antibody. The light intensity is related to the amount of the pre-coated anti-IgG antibody and working as on-chip QC indicator. The total assay time will be approximately 20 minutes for this troponin assay. Table 2 illustrates the typical assay procedure and the motions in the system.

TABLE 2

Assay procedure and system actions for conduct a single analyte troponin assay in POCT system

| Assay step | System action |
|---|---|
| Detection antibody reconstitution | Pick up tip, aspirate buffer from reagent pack, dispense and mix in well A2 |
| Mix sample with detection antibody | Aspirate reconstituted detection antibody from A2 and dispense to well A3, aspirate sample from A1 and dispense to well A3, mix |
| Load mixture in detection chamber, high and low control chamber | Aspirate mixture from A3 and dispense to detection chamber, high and low control chamber (B1-B3). |
| Repeat load mixture in detection chamber* | Aspirate mixture from A3 and dispense to detection chamber (B1) for 10 times |
| Load wash buffer | Replace the new tip, aspirate wash buffer from reagent pack, dispense to B1-B3 |
| Load substrate | Aspirate substrate from reagent pack, dispense to B1-B3 |
| Read | Measure the light intensity from B1-B3 by detector module |
| Calculate and present the concentration | The concentration will be calculated and present on display |

Figure 5:
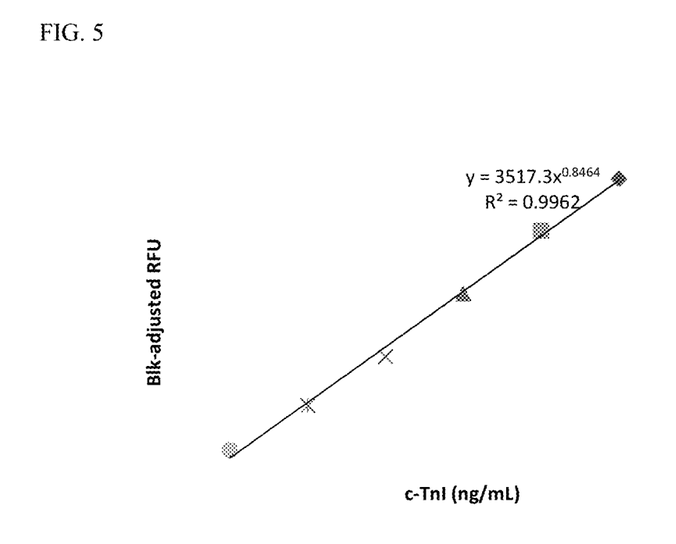
FIG. 5 shows a typical standard curve for a c-TnI assay performed using a preferred embodiment of a POCT assay system according to the present invention.

*Assay sensitivity can be improved by repeat loading antigen into the microfluidic detection chamber
An example of a standard curve for a Troponin assay is shown in FIG. 5, in the POC system of the present invention.

Multi-Analyte Assay in Accordance with Another Preferred Embodiment of the Present Invention Multiple analytes may be measured simultaneously using one cartridge, in accordance with a further preferred embodiment of the present invention. Multiple detection chambers will be pre-coated with different capture antibodies in a microchannel of each well. The detection antibodies will be mixed together and lyophilized in one storage well. Table 3 shows a preferred chamber layout for an example of a three-analyte assay performed in accordance with the teachings of the present invention. Table 4 illustrates the typical assay procedure and the motions in the system.

TABLE 3

Chamber layout for the cartridge in multi-analyte assay

| Storage/mixing chamber | | | Detection chamber | | | | |
|---|---|---|---|---|---|---|---|
| A1 | A2 | A3 | B1 | B2 | B3 | B4 | B5 |
| Well for Sample loading | Well contains lyophilized detection | Well for mixing sample with | Detection chamber, pre-coated | Detection chamber, pre-coated | Detection chamber, pre-coated | High control, pre-coated with high | Low control, pre-coated with low |

TABLE 3-continued

Chamber layout for the cartridge in multi-analyte assay

| Storage/mixing chamber | | | Detection chamber | | | | |
| --- | --- | --- | --- | --- | --- | --- | --- |
| A1 | A2 | A3 | B1 | B2 | B3 | B4 | B5 |
| antibody mixture | reconstituted detection antibody | capture antibody #1 | capture antibody #2 | capture antibody #3 | concentration anti-IgG antibody | concentration anti-IgG antibody | |

TABLE 4

Assay procedure and system actions for conduct a three-analyte assay in accordance with a preferred POCT assay system of the invention (references are to Table 3)

| Assay step | System action |
| --- | --- |
| Detection antibody reconstitution | Pick up tip, aspirate buffer from reagent pack, dispense and mix in well A2 |
| Mix sample with detection antibody | Aspirate reconstituted detection antibody from A2 and dispense to well A3, aspirate sample from A1 and dispense to well A3, mix |
| Load mixture in detection chambers, high and low control chamber | Aspirate mixture from A3 and dispense to each detection chamber (B1-B3), high and low control chamber (B4, B5). |
| Repeat load mixture in detection chamber ( if needed) | Aspirate mixture from A3 and dispense to each detection chamber (B1-B3) for certain number of times |
| Load wash buffer | Replace the new tip, aspirate wash buffer from reagent pack, dispense to B1-B5 |
| Load substrate | Aspirate substrate from reagent pack, dispense to B1-B5 |
| Read | Measure the light intensity from B1-B3 by detector module |
| Calculate and present the concentrations | The concentration for each analyte will be calculated and present on display |

Wide Dynamic Range Assay—HCG Assay Performed in Accordance with an Additional Preferred Embodiment of the POCT Assay System of the Invention A dynamic range for a typical assay in the POCT assay system of the present invention is no more than 3-log. In order to measure analytes with concentrations cross 4 or 5 log, such as human HCG in pregnant women, an on-board dilution can be used in the system. Table 5 shows chamber layout for a typical HCG wide dynamic range assay performed in accordance with another preferred embodiment of the present invention. One empty well will be used to dilute the sample with reconstituted detection antibody solution. Two detection chambers with same capture antibody pre-coated will be used to detect the undiluted and diluted sample. Table 6 illustrates the typical assay procedure and the motions in the system.

TABLE 5

Chamber layout for the cartridge in an embodiment of a wide dynamic range assay performed in accordance with the present invention

| Storage/mixing/dilution chamber | | | | Detection chamber | | | |
| --- | --- | --- | --- | --- | --- | --- | --- |
| A1 | A2 | A3 | A4 | B1 | B2 | B3 | B4 |
| Well for Sample loading | Well contains lyophilized detection antibody mixture | Well for mixing sample with reconstituted detection antibody | Dilution well 1 | Detection chamber, pre-coated capture antibody | Detection chamber, pre-coated capture antibody | High control, pre-coated with high concentration anti-IgG antibody | Low control, pre-coated with low concentration anti-IgG antibody |

TABLE 6

Assay procedure and system actions for conduct a wide-dynamic range assay in an embodiment of a POCT assay system of the invention

| Assay step | System action |
| --- | --- |
| Prepare dilution buffer, step 1 | Pick up tip, aspirate buffer from reagent pack, dispense in well A4 |
| Detection antibody reconstitution | Aspirate buffer from reagent pack, dispense and mix in well A2 |
| Prepare dilution buffer, step 2 | Aspirate reconstituted antibody from A2, dispense and mix in well A4 |
| Mix sample with detection antibody | Aspirate reconstituted detection antibody from A2 and dispense to well A3, aspirate sample from A1 and dispense to well A3, mix |

TABLE 6-continued

Assay procedure and system actions for conduct a wide-dynamic range assay in an embodiment of a POCT assay system of the invention

| Assay step | System action |
|---|---|
| Dilute sample&antibody mixture | Aspirate mixture from well A3, dispense and mix in well A4 |
| Load diluted sample mixture in detection chamber | Aspirate diluted mixture from A4 and dispense to detection chamber B1 |
| Load undiluted sample mixture in detection chamber, high and low control chamber | Aspirate mixture from A3 and dispense to detection chamber B2, high and low control chamber (B3, B4) |
| Load wash buffer | Replace the new tip, aspirate wash buffer from reagent pack, dispense to B1-B4 |
| Load substrate | Aspirate substrate from reagent pack, dispense to B1-B4 |
| Read | Measure the light intensity from B1-B2 by detector module |
| Calculate and present the concentrations | The concentration for will be calculated and present on display |

Note:
There is no repeat loading of sample mixture in the HCG assay, however it can be added if needed.

Note: There is no repeat loading of sample mixture in the HCG assay, however it can be added if needed.

Figure 6:
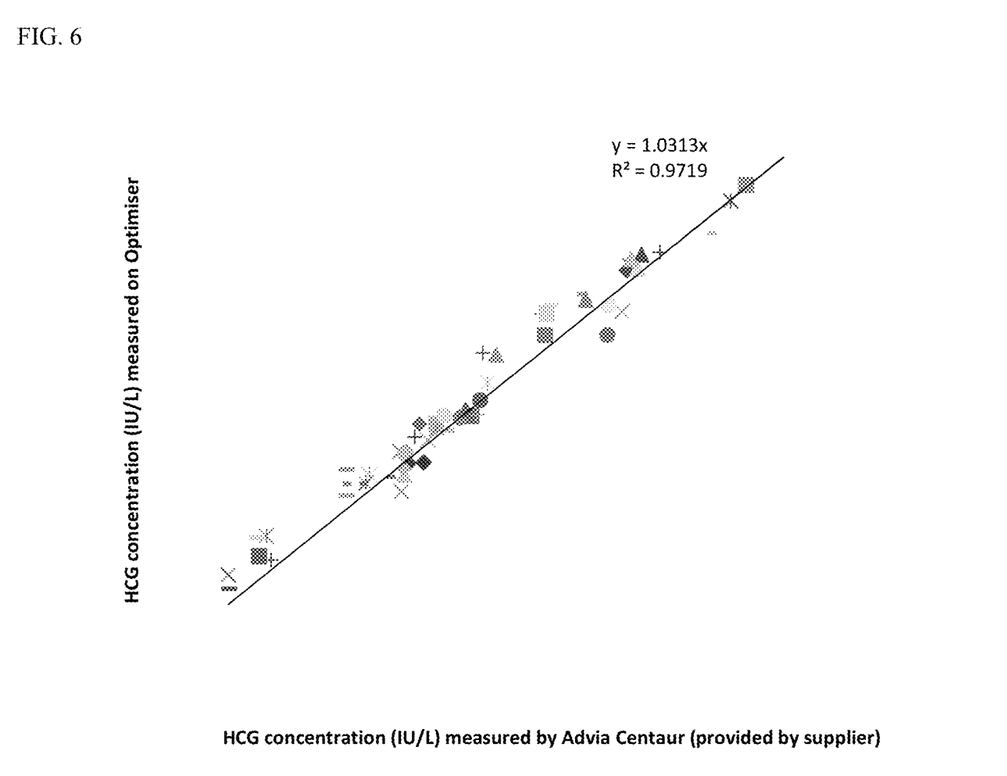
FIG. 6 shows a correlation curve of measured HCG concentration from human serum sample in comparison between a preferred embodiment of a POCT assay system of the present invention and that measured using a commercially available Advia Centaur bench top system.

In order to further illustrate the advantages of the present invention, comparison of a correlation curve of measured HCG concentration from human serum sample between a prototype POCT assay system in accordance with the present invention and a largely conventional, commercially available bench top assay system (the Advia Centaur), is shown in FIG. 6.

Additional objects and advantages, as well as variations and modifications, of the present invention will be apparent to those skilled in the art from the description of the invention herein, and all of the foregoing are intended to be within the scope of the invention.

What is claimed is:

1. A point of care testing assay system comprising:
    a microfluidic testing cartridge comprising:
        a single row of chambers comprising:
            a first chamber for storing a sample;
            a second chamber including lyophilized detection antibody;
            a mixing chamber; and
            a plurality of detection chambers,
    a reagent pack including buffers and substrate; and
    a precision pipettor configured to:
        transfer the buffers from the reagent pack to the second chamber to reconstruct the detection antibody;
        aspirate a sample in the first chamber and dispense the aspirated sample to the mixing chamber;
        aspirate the reconstructed detection antibody in the second chamber and dispense the aspirated reconstructed detection antibody to the mixing chamber; and
        aspirate the mixture of the sample and reconstructed detection antibody in the mixing chamber and dispense the aspirated mixture to the plurality of detection chambers
    a detection module configured to detect luminescence of the plurality of detection chambers;
    a horizontal motion stage configured to move the microfluidic testing cartridge; and
    a vertical motion stage configured to move the precision pipettor or the detection module,
    wherein each of the plurality of detection chambers includes a single well and a single microfluidic channel connected below the single well,
    one or more of the plurality of detection chambers is pre-coated with capture antibodies,
    top surfaces of the first chamber, the second chamber, the mixing chamber, and the plurality of detection chambers are circularly shaped, equally sized, and linearly arranged on the microfluidic testing cartridge, and
    wherein the microfluidic channel is formed in a spiral pattern and a central portion of each microfluidic channel is connected to a bottom portion of each well.

2. The point of care testing assay system of claim 1, wherein the plurality of detection chambers include a first chamber pre-coated with first anti-IgG antibody and a second chamber pre-coated with second anti-IgG antibody, wherein concentration of first anti-IgG antibody is greater than concentration of the second anti-IgG antibody.

3. The point of care testing assay system of claim 1, wherein the two or more storage and mixing chambers includes a chamber for the sample, a chamber containing the one or more detection antibodies, and a chamber for mixing the sample and the one or more detection antibodies,
    the chamber containing the one or more detection antibodies is adjacent to the chamber for the sample, and
    the chamber for mixing the sample and the one or more detection antibodies is adjacent to the chamber containing the one or more detection antibodies.

4. The point of care testing assay system of claim 1, wherein one of the plurality of detection chambers is pre-coated with a first antibody, and another of the plurality of detection chambers is pre-coated with a second antibody, and
    the first antibody is different from the second antibody.

5. The point of care testing assay system of claim 1, wherein two or more storage and mixing chambers include a dilution well.

6. The point of care testing assay system of claim 1, wherein the vertical motion stage is configured to move the precision pipettor or the detection module relative to the microfluidic testing cartridge independent of operations of the horizontal motion stage.

* * * * *